(12) United States Patent
Lemchen et al.

(10) Patent No.: US 10,548,691 B2
(45) Date of Patent: Feb. 4, 2020

(54) SYSTEM AND METHOD FOR ORDERING AND MANUFACTURING CUSTOMIZED ORTHODONTIC APPLIANCES AND PRODUCT

(71) Applicants: Marc Lemchen, New York, NY (US); Jim Wright, Williamsville, NY (US); Michael Wright, Clarence Center, NY (US); Todd Blankenbecler, Atlanta, GA (US)

(72) Inventors: Marc Lemchen, New York, NY (US); Jim Wright, Williamsville, NY (US); Michael Wright, Clarence Center, NY (US); Todd Blankenbecler, Atlanta, GA (US)

(73) Assignee: EasyRx, LLC., Atlanta, GA (US)

( * ) Notice: Subject to any disclaimer, the term of this patent is extended or adjusted under 35 U.S.C. 154(b) by 0 days.

(21) Appl. No.: 15/856,958

(22) Filed: Dec. 28, 2017

(65) Prior Publication Data
US 2018/0116763 A1     May 3, 2018

Related U.S. Application Data

(62) Division of application No. 15/072,198, filed on Mar. 16, 2016, now Pat. No. 10,299,891.

(51) Int. Cl.
*A61C 7/00*     (2006.01)
*G06F 19/00*    (2018.01)
(Continued)

(52) U.S. Cl.
CPC .......... *A61C 7/002* (2013.01); *G06F 19/328* (2013.01); *G06F 19/3456* (2013.01);
(Continued)

(58) Field of Classification Search
CPC ... A61C 7/002; G06F 19/322; G06F 19/3456; G06F 19/328
See application file for complete search history.

(56) References Cited

U.S. PATENT DOCUMENTS 6,733,289 B2   5/2004   Manemann
8,121,718 B2   2/2012   Rubbert
(Continued)

OTHER PUBLICATIONS

Getting started with easyrx, a cloud network for orthodontists and their labs, Published on Oct. 10, 2012. (https://www.youtube.com/watch?v=l8xsC6AXiM0).*

(Continued)

*Primary Examiner* — Vincent H Tran
(74) *Attorney, Agent, or Firm* — Marcus C. Dawes; Daniel L. Dawes

(57) ABSTRACT

A prescription management system is used by an orthodontic or dental lab and a plurality of prescribing users who send prescriptions for customized orthodontic or dental appliances to the lab. The prescriptions are stored in a database selectively accessible by the lab and plurality of prescribing users. A digital workspace is provided in the system in which the lab or prescribing users may create designs for the customized appliances. The designs of the appliances are stored in the database. A tracking record of fabrication of the appliances is stored in the database. A plurality of billings are simultaneously generated in response to the submissions and storage of the prescriptions, the designs of the customized appliances and the fabrication of the designed customized appliances.

3 Claims, 14 Drawing Sheets

(51) Int. Cl.
*G16H 10/60* (2018.01)
*G16H 50/00* (2018.01)
*G16H 20/00* (2018.01)
*G16H 20/40* (2018.01)
*G16H 40/20* (2018.01)
*G16H 20/10* (2018.01)

(52) U.S. Cl.
CPC ............ *G16H 10/60* (2018.01); *G16H 20/00* (2018.01); *G16H 20/10* (2018.01); *G16H 20/40* (2018.01); *G16H 40/20* (2018.01); *G16H 50/00* (2018.01)

(56) References Cited

U.S. PATENT DOCUMENTS

| | | | |
|---|---|---|---|
| 8,185,417 B1 | 5/2012 | Brown | |
| 2005/0191594 A1* | 9/2005 | Taub | A61C 7/00 433/24 |
| 2006/0078842 A1* | 4/2006 | Sachdeva | A61C 7/00 433/24 |
| 2008/0096151 A1* | 4/2008 | Cinader, Jr. | G16H 50/50 433/24 |
| 2008/0195418 A1 | 8/2008 | Parker | |
| 2009/0017410 A1* | 1/2009 | Raby | A61C 7/002 433/2 |
| 2010/0223034 A1* | 9/2010 | Imgrund | A61C 7/00 703/1 |
| 2013/0060532 A1* | 3/2013 | Clausen | A61C 13/08 703/1 |
| 2014/0067335 A1* | 3/2014 | Andreiko | A61C 7/002 703/1 |
| 2015/0351871 A1* | 12/2015 | Chishti | A61C 7/00 433/6 |
| 2016/0175068 A1* | 6/2016 | Cai | A61C 7/002 700/98 |

OTHER PUBLICATIONS

Introducing easyrx—a cloud network for orthodontists and their labs (https://www.youtube.com/watch?v=WawnU97WU2s), Published on Oct. 10, 2012.*

Easyrx rx walkthrough.mp4 (https://www.youtube.com/watch?v=SgRLDtkpDM4), Published on Jan. 22, 2013.*

Website, Orthodontic Products Online, EasyRx releases its cloud-based appliance prescription management system, Oct. 15, 2012, internal pp. 1-3, www.orthodonticproductsonline.com/2012/10/orthodent-laboratory-releases-cloud-based-easyrx.

* cited by examiner

R  UPPER  L

R  UPPER  L

L  LOWER  R

L  LOWER  R

Comments | Resets | Templates   Study Model   ClearLign   Uploads
Note: Resets for ClearLign (clear aligner) cases must be added and removed through the ClearLign tab.
Resets
  R: 8 7 6 [5] 4 3 2 1  L: 1 2 3 4 5 6 7 8
  R: 8 7 6 5 4 3 2 1  L: 1 2 [3] 4 5 6 7 8

Diagnostic Setup
Resets
  R: 8 7 6 5 4 3 2 1  L: 1 2 3 4 5 6 7 8
  R: 8 7 6 5 4 [3] 2 1  L: 1 2 3 4 5 6 7 8
Extract
  R: 8 7 [6] 5 4 3 2 1  L: 1 2 3 4 5 6 7 8
  R: 8 7 6 5 4 3 2 1  L: 1 2 3 4 5 6 7 8 easyrx

Dashboard | Patients | Templates | Prescriptions

Practice Dashboard
Dashboard

Saved Prescriptions (Not Yet Submitted)

[Search]

| ID ▼ | Patient | Date Created | |
|---|---|---|---|
| 21354 | George Washington | 1/19/12 | view edit delete |
| 21339 | Smith John | 1/19/12 | view edit delete |
| 19463 | Don Johnson | 12/9/11 | view edit delete |
| 19462 | Michael Knight | 12/9/11 | view edit delete |
| 18715 | internet explorer | 11/22/11 | view edit delete |
| 18714 | internet explorer | 11/22/11 | view edit delete |
| 18542 | Spam Bohanan | 11/18/11 | view edit delete |
| 16175 | Abraham Lincoln | 9/28/11 | view edit delete |
| 16019 | Abraham Lincoln | 9/24/11 | view edit delete |
| 14538 | Abraham Lincoln | 8/21/11 | view edit delete |

‹ Prev  [1]  2  3  Next ›

Submitted Prescriptions

[Search]

| ID ▼ | Patient | Doctor | Date Created | Date Needed | |
|---|---|---|---|---|---|
| 18596 | John Labatts | James Wright | 11/21/11 | 1/26/12 | view |
| 9407 | John Smith | James Wright | 5/3/11 | 5/18/11 | view |
| 6859 | Mr. T | James Wright | 3/7/11 | 3/25/11 | view |
| 5429 | Jack Black | James Wright | 3/6/11 | 3/10/11 | view |

*FIG. 2* easyrx

Dashboard | Patients | Templates | Prescriptions

Manage Patients
Dashboard >> Manage Patients >> View Patient

| First Name *Smith* | Last Name *John* |
|---|---|
| Date of Birth *5/9/93* | |

Edit  List

Prescriptions

[                    ] [Search]

| ID | Date Created | |
|---|---|---|
| 21339 | 1/19/12 | view edit delete |

[Create Prescription⇒]

File Upload(s)

Select the "Add File(s)" button or drag and drop a file (or files) on to this page to upload!

[Add File(s)⇒]

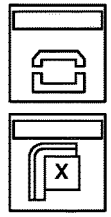

21339/012345_Pre Tx_Maxillar.stl     5.62 MB     

21339/November 2011.xls     29.18 KB     

*FIG. 3*

Parts Library — 28

Click on category to expand
then click and drag part to canvas

Search...

Search Results ◁
Removables ▽
  Labial Bows ◁
  Clasping ▽

Adams Clasp — 30

Arrow Clasp

Ball Clasp

Buccal Tube Clasp

Circumferential Clasp

Continuous Rest

Hook Clasp

Lingual Clasp

Rest

Soldered C-Clasp

Spur

Springs ◁
  Auxiliary ◁
  Spring Aligners ◁
  Functionals ◁
  Invisibles ◁
  Acrylic
Fixed ◁
Herbst ◁
Splints ◁

*FIG. 5*

Prescription ID: 21499
Patient: Smith John

Clear All Parts

- right click options
- click and drag

R UPPER L     L LOWER R

Alternate Bow:    close
[ Choose ⬍ ]
Wire Gauge: [ Choose ⬍ ]

[ Colors ]     [ Colors ]

| | | | |
|---|---|---|---|
| Labial Bow | ✏ edit | ⊗ delete | comment |
| Acrylic | ✏ edit | ⊗ delete | comment |
| Adams Clasp | ✏ edit | ⊗ delete | comment |
| Adams Clasp | ✏ edit | ⊗ delete | comment |
| Rest | ✏ edit | ⊗ delete | comment |

Comments   Resets   Templates   Study Model   ClearLign   Uploads

FIG. 6

| Comments | Resets | Templates | Study Model | ClearLign | Uploads |

FIG. 7

| Comments | Resets | Templates —40 | Study Model | ClearLign | Uploads |

| | Arch | Template Name |
|---|---|---|
| add | both | bionator |
| add | lower | Lower Retainer |
| add | upper | RPE (bands on 5's) |
| add | both | Upper and lower standard hawleys |
| add | upper | Upper Anterior Springs 2-2 |
| add | upper | Upper Hawley with ball clasps |
| add | upper | Upper Hawley, Adams on 6's |

| Comments | Resets | Templates | Study Model | ClearLign | Uploads |

Select the "Add File(s)" button or drag and drop a file (or files) on to this page to upload!

Add File(s) ⇒

RPE.JPG          58          113.73 KB    🗑

012345_Pre Tx_Maxillar.stl          5.62 MB    🗑

Cancel   Save   Save as Template   Delete          Proceed to Checkout ▶

 Success!
- Prescription Submitted.
- Please print this page and send it with any models or impressions. Click Here To Print
- Prescription ID: 21499

Prescription ID: 21499  
Practice: Mike Wright Practice  
Doctor: James Wright  
Patient: Smith John Date Needed: 1/28/12  
adress:  
6325 Sheridan Drive  
Williamsville, New York 14221  
United States  
Phone #: 716-839-1900

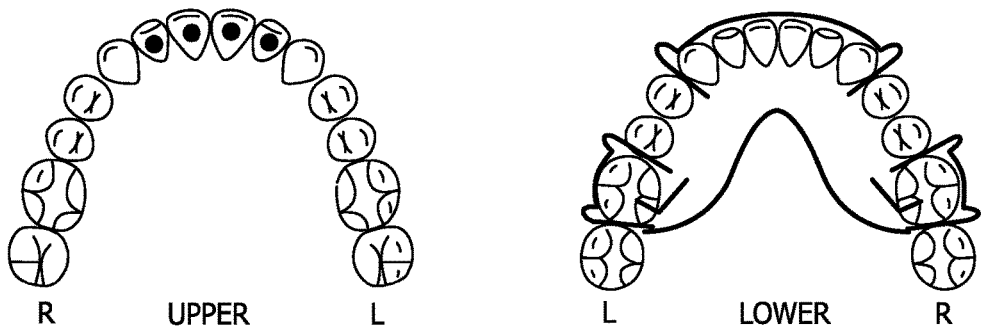

Color: n10 Blueberry

Comments  add comments
 No comments.

Parts without Options
 Labial Bow (3ll), Acrylic (6lil), Adams Clasp (6ll), Adams Clasp (6lr), Rest (6ll), Rest (6lr)

ClearLign
 Type:
 Number of Trays:
 Teeth to be Aligned:  R: 8 7 6 5 4 3 [2][1]  L: [1][2] 3 4 5 6 7 8
 R: 8 7 6 5 4 3 2 1  L: 1 2 3 4 5 6 7 8
 Stripping (IPR):

Cancel  (Print ⇨)  (Export PDF ⇨) — 64

*FIG. 12*

Prescription Check-In
Dashboard >> Prescription Check-In

Scan the prescription barcode or type the prescription ID and click the "Submit" button to start the check-in process. If a prescription has not been created in the system use the "Written Prescription" button.

Prescription ID

[            ]     [ Written Prescription ]

[ Submit ⇨ ]

*FIG. 13*

Prescription Completion Log
Dashboard >> Prescription Completion Log

Department
[ Acrylic Station ⇵ ]

Scan one or more prescription barcodes, or type the prescription ID.
[            ]

Add Another  [ Submit ⇨ ]

*FIG. 14* easyrx

Dashboard  Practices  Patients  Check-in  Check-out  | QuickBooks |  Prescriptions

QuickBooks Export ▽  QuickBooks Export
Shipping Report  Dashboard >> QuickBooks Export
Archived Import File Folder

| Rx ID | Line Item | Price | QuickBooks Item Number |
|---|---|---|---|
| 15822 | Fixed 3D Quad-helix, Band and installation | $70.65 | 4010 Sales Fixed Tax |

[ Generate File ]

Fixed: 3D Quad-helix, Band and Installation
| Description | Price | Quanity | Total |
|---|---|---|---|
| 3D Quad-helix | $53.25 | 1 | $53.25 |
| Band and Installation | $8.70 | 2 | $17.40 |
|  |  | Total | $70.85 |

*FIG. 15* easyrx

Dashboard  Accounts  | Parts |  Patients  Prescriptions  Templates
               70      68                    66          40

Manage Parts ▽  Manage Parts
Tree View  Dashboard >> Manage Parts
Study Model & Resets
Digital Study Models
ClearLign
Part Option
Bands
Charge All Part Prices

| Part Name ▽ | Price | Status | | |
|---|---|---|---|---|
| "W" Arch | $41.60 | Active | view | edit |
| "W" Arch w/ Habit Crib | $62.90 | Active | view | edit |
| .0175 Coaxial | $25.20 | Active | view | edit |
| .0175 Coaxial w/ Tray | $60.75 | Active | view | edit |
| 3-way Expansion Screw | $39.25 | Active | view | edit |
| 3D Lingual Arch | $44.00 | Active | view | edit |
| 3D Quad-helix | $53.25 | Active | view | edit |
| 3x3 Bonded | $25.20 | Active | view | edit |
| 3x3 Krouse | $61.10 | Active | view | edit |
| 3x3 w/ Bonding Tray | $60.75 | Active | view | edit |

◁ Prev  [1] 2 3 4 5 ... 18  Next ▷

*FIG. 16*

R  UPPER  L

L  LOWER  R

SYSTEM AND METHOD FOR ORDERING AND MANUFACTURING CUSTOMIZED ORTHODONTIC APPLIANCES AND PRODUCT

BACKGROUND

Field of the Technology

The invention relates to the field of ordering, manufacturing, billing and documenting the process of customized orthodontic and dental appliances.

Description of the Prior Art

In the orthodontic laboratory, prescriptions have been traditionally provided to the lab with a graphical representation of the design of the appliance used for treatment. A typical paper prescription is filled out, with a hand drawn design and sent to the lab with a dental impression or cast for fabrication. Once received, the patient information is entered into a database and the case is scheduled for the design review. A designer reviews the paper prescription and makes any needed modifications for the technicians, who will be making the appliance and for the billing department to bill for the parts and services rendered in response to the prescription.

Once the appliance has been designed and then fabricated, the billing department makes a copy of the prescription and manually bills out the appliance. Since each appliance is made up of multiple parts with very specific designs, the bill is detailed and manually broken down to illustrate the parts of the retainer. The paper prescriptions are then filed and stored away for reference.

BRIEF SUMMARY

The illustrated embodiments of the invention include within their scope a method of prescription management for use with an orthodontic or dental lab and a prescribing user. The method includes the steps of: submitting a prescription from the prescribing user for a customized orthodontic or dental appliance to the orthodontic or dental lab; storing the prescription; designing the customized orthodontic or dental appliance in response to the prescription; fabricating the designed customized orthodontic or dental appliance; and simultaneously creating a billing in response to submitting the prescription, storing the prescription, designing the customized orthodontic or dental appliance and fabricating the designed customized orthodontic or dental appliance.

As will become apparent in the detailed description below the method is collectively performed by the labs and the prescribing users.

The method further includes the steps of simultaneously creating a digital tracking record in response to submitting the prescription, storing the prescription, designing the customized orthodontic or dental appliance and fabricating the designed customized orthodontic or dental appliance.

The method further includes the step of simultaneously creating a documentary record in response to submitting the prescription, storing the prescription, designing the customized orthodontic or dental appliance and fabricating the designed customized orthodontic or dental appliance.

The method further includes the step of selectively reviewing the stored prescription corresponding to prescribing user.

The step of fabricating the designed customized orthodontic or dental appliance includes the step of including selected parts from a listing of a plurality of categories of parts for inclusion and placement in the customized orthodontic or dental appliance, while simultaneously tracking and recording the inclusion of the selected parts to create the billing therefor in response to the submitted prescription.

The step of designing the customized orthodontic or dental appliance in response to the prescription includes the steps of creating a template of the customized orthodontic or dental appliance, and storing the template for later access for modification of the customized orthodontic or dental appliance.

The step of submitting a prescription from the prescribing user for a customized orthodontic or dental appliance to the orthodontic or dental lab includes the step of submitting a prescription from a plurality of prescribing users for a corresponding plurality of customized orthodontic or dental appliances to a plurality of corresponding orthodontic or dental labs, where storing the prescription includes the step of storing a corresponding plurality of subscriptions, where designing the customized orthodontic or dental appliance in response to the prescription includes the step of designing a corresponding plurality of customized orthodontic or dental appliances in response to the corresponding prescriptions, where fabricating the designed customized orthodontic or dental appliance includes the step of fabricating a corresponding plurality of designed customized orthodontic or dental appliances, and where simultaneously creating a billing in response to submitting the prescription, storing the prescription, designing the customized orthodontic or dental appliance and fabricating the designed customized orthodontic or dental appliance includes the step of creating a corresponding plurality of billings in response to submitting the prescriptions, storing the prescriptions, designing the customized orthodontic or dental appliances and fabricating the designed customized orthodontic or dental appliances.

The illustrated embodiment can also be characterized as a method of providing a prescription management system for use with a plurality of orthodontic or dental labs and a plurality of prescribing users. The embodiment includes the steps of receiving a plurality of prescriptions from the plurality of prescribing users for customized orthodontic or dental appliances to be provided to the prescribing users by the plurality of orthodontic or dental labs, storing the prescriptions in a database selectively accessible by the plurality of orthodontic or dental labs and plurality of prescribing users, providing a digital workspace in which each of the plurality of orthodontic or dental labs or prescribing users may create a plurality of corresponding designs of the customized orthodontic or dental appliances in response to the corresponding prescriptions, storing the plurality of corresponding designs of the customized orthodontic or dental appliances in the database selectively accessible by the plurality of orthodontic or dental labs and plurality of prescribing users, tracking and storing a record of fabrication of the plurality of customized orthodontic or dental appliances by the plurality of corresponding orthodontic or dental labs in the database selectively accessible by the plurality of orthodontic or dental labs and plurality of prescribing users, and simultaneously creating a plurality of corresponding billings in response to the plurality of submissions and storage of the plurality of corresponding prescriptions, the plurality of designs of the customized orthodontic or dental appliances and the fabrication of the plurality of designed customized orthodontic or dental appliances.

The method further includes the step of communicating the prescription management system to a cloud storage system. The steps of storing the prescriptions in a database, storing the plurality of corresponding designs of the customized orthodontic or dental appliances in the database, and tracking and storing a record of fabrication of the plurality of customized orthodontic or dental appliances by the plurality of corresponding orthodontic or dental labs in the database includes the steps of storing the prescriptions in a database in the cloud storage system, storing the plurality of corresponding designs of the customized orthodontic or dental appliances in the database in the cloud storage system, and tracking and storing a record of fabrication of the plurality of customized orthodontic or dental appliances by the plurality of corresponding orthodontic or dental labs in the database in the cloud storage system.

The step of tracking and storing a record of fabrication of the plurality of customized orthodontic or dental appliances includes the step of including tracking and storing of selected parts from a listing of a plurality of categories of parts for inclusion and placement in the customized orthodontic or dental appliance, while simultaneously tracking and recording the inclusion of the selected parts to create the billing therefor in response to the submitted prescription.

The step of providing a digital workspace for designing the customized orthodontic or dental appliance in response to the prescription includes the step of providing the digital workspace to create a template of the customized orthodontic or dental appliance, and storing the template for later access for modification of the customized orthodontic or dental appliance.

The illustrated embodiments also include within their scope a method of providing a prescription management system for use with an orthodontic or dental lab and a plurality of prescribing users. The method includes the steps of receiving a plurality of prescriptions from the plurality of prescribing users for customized orthodontic or dental appliances to be provided to the prescribing users by the orthodontic or dental lab, storing the prescriptions in a database selectively accessible by the orthodontic or dental lab and plurality of prescribing users, providing a digital workspace in which the orthodontic or dental lab or prescribing users may create a plurality of corresponding designs of the customized orthodontic or dental appliances in response to the corresponding prescriptions, storing the plurality of corresponding designs of the customized orthodontic or dental appliances in the database selectively accessible by the orthodontic or dental lab and plurality of prescribing users, tracking and storing a record of fabrication of the plurality of customized orthodontic or dental appliances by the orthodontic or dental lab in the database selectively accessible by the orthodontic or dental lab and plurality of prescribing users, and simultaneously creating a plurality of corresponding billings in response to the plurality of submissions and storage of the plurality of corresponding prescriptions, the plurality of designs of the customized orthodontic or dental appliances and the fabrication of the plurality of designed customized orthodontic or dental appliances.

The illustrated embodiment include a prescription management system for use with an orthodontic or dental lab and a plurality of prescribing users. The system includes means for receiving a plurality of prescriptions from the plurality of prescribing users for customized orthodontic or dental appliances to be provided to the prescribing users by the orthodontic or dental lab, means for storing the prescriptions in a database selectively accessible by the orthodontic or dental lab and plurality of prescribing users, means for providing a digital workspace in which the orthodontic or dental lab or prescribing users may create a plurality of corresponding designs of the customized orthodontic or dental appliances in response to the corresponding prescriptions, means for storing the plurality of corresponding designs of the customized orthodontic or dental appliances in the database selectively accessible by the orthodontic or dental lab and plurality of prescribing users, means for tracking and storing a record of fabrication of the plurality of customized orthodontic or dental appliances by the orthodontic or dental lab in the database selectively accessible by the orthodontic or dental lab and plurality of prescribing users, and means for simultaneously creating a plurality of corresponding billings in response to the plurality of submissions and storage of the plurality of corresponding prescriptions, the plurality of designs of the customized orthodontic or dental appliances and the fabrication of the plurality of designed customized orthodontic or dental appliances.

The various means disclosed include a network of computers controlled by a computer server communicated through the internet with computer systems in the plurality of orthodontic or dental labs and the plurality of prescribing users. The computer server and networked computers are controlled by software instructions stored on a tangible memory medium, which control the circuitry, memories and displays of the server and computer systems, which are organized by the software as modules with input/output screens for performing the defining functions of the means. The intercommunication of the server with the plurality computer systems, including cloud storage, is well established in conventional internet communication protocols and computer architectures.

The prescription management system further includes means for communicating the prescription management system to a cloud storage system, and where the means for storing the prescriptions in a database, the means for storing the plurality of corresponding designs of the customized orthodontic or dental appliances in the database, and the means for tracking and storing a record of fabrication of the plurality of customized orthodontic or dental appliances by the orthodontic or dental lab in the database comprises means for storing the prescriptions in a database in the cloud storage system, means for storing the plurality of corresponding designs of the customized orthodontic or dental appliances in the database in the cloud storage system, and means for tracking and storing a record of fabrication of the plurality of customized orthodontic or dental appliances by the orthodontic or dental lab in the database in the cloud storage system.

The means for tracking and storing a record of fabrication of the plurality of customized orthodontic or dental appliances includes means for including tracking and storing of selected parts from a listing of a plurality of categories of parts for inclusion and placement in the customized orthodontic or dental appliance, while simultaneously tracking and recording the inclusion of the selected parts to create the billing therefor in response to the submitted prescription.

The means for providing a digital workspace for designing the customized orthodontic or dental appliance in response to the prescription includes means for providing the digital workspace to create a template of the customized orthodontic or dental appliance, and means for storing the template for later access for modification of the customized orthodontic or dental appliance.

Another embodiment includes a method for controlling a design in a computer for an assembly of orthodontic parts in an orthodontic appliance. The method includes the steps of defining a rule of movement and behavior which is permitted for each one of a plurality of orthodontic parts with respect to at least one tooth or other one of the plurality of orthodontic parts; and moving, placing, orienting or removing the orthodontic parts in a graphic image of the design in compliance with the rule defined for the orthodontic parts during the assembly of orthodontic parts into the orthodontic appliance.

The method further includes converting the design as assembled into computer assisted manufacturing instructions to assembly the orthodontic appliance from the plurality of orthodontic parts.

The step defining a rule of movement and behavior which is permitted for each one of a plurality of orthodontic parts with respect to at least one tooth or other one of the plurality of orthodontic parts includes the steps of defining at least one anchor for each part and a plurality of magnet points at which the at least one anchor may be positioned, defining whether or not the at least one anchor can be removed from the design, defining whether the at least one anchor is one of two anchor buddies or an anchor pair with coupled movement with another anchor, or defining an orientation of each part.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The disclosure can be better visualized by turning now to the following drawings wherein like elements are referenced by like numerals.

BRIEF DESCRIPTION OF THE DRAWINGS

FIGS. 1a and 1b hand sketches created by an orthodontist for an upper and lower retainer respectively and FIGS. 1c and 1d are the corresponding customized designs created by the designer in the lab in response to the orthodontist's hand sketched prescription.

FIG. 2 is an illustrative example of a screen shot of the Practice Dashboard of the illustrated embodiment.

FIG. 3 is an illustrative example of a screen shot of the Manage Patients module of the illustrated embodiment.

FIG. 5 is an illustrative example of a screen shot of the Parts Library of the illustrated embodiment, illustrating in this example the pull down listing of the Clasping part.

FIG. 6 is an illustrative example of a screen shot of a prescription for a specific patient as used in the illustrated embodiment.

FIG. 7 is an illustrative example of a screen shot of the action tabs provided below the canvas as used in the illustrated embodiment.

FIG. 9 is an illustrative example of a screen shot of the Templates action tabs provided below the canvas as used in the illustrated embodiment.

FIG. 11 is an illustrative example of a screen shot of the Uploads action tabs provided below the canvas as used in the illustrated embodiment.

FIG. 12 is an illustrative example of a screen shot of the Confirmation Screen as used in the illustrated embodiment.

FIG. 13 is an illustrative example of a screen shot of the Prescription Check-In as used in the illustrated embodiment.

FIG. 14 is an illustrative example of a screen shot of the Prescription Completion Log as used in the illustrated embodiment.

FIG. 15 is an illustrative example of a screen shot of the Confirmation Screen as used in the illustrated embodiment.

FIG. 16 is an illustrative example of a screen shot of the administrative screen relating to the Manage Parts module as used in the illustrated embodiment.

The disclosure and its various embodiments can now be better understood by turning to the following detailed description of the preferred embodiments which are presented as illustrated examples of the embodiments defined in the claims. It is expressly understood that the embodiments as defined by the claims may be broader than the illustrated embodiments described below.

DETAILED DESCRIPTION OF THE PREFERRED EMBODIMENTS

The illustrated system and method, offered under the commercial name, Easyprescription™, is a web based application that is designed to create and manage orthodontic laboratory prescriptions within a dental clinic as well as the lab. The system coordinates and facilitates processing of orthodontic prescriptions and their fulfillment between a multiplicity of dental offices or clinics and a multiplicity of orthodontic or dental labs. In one sense, it is a digital delivery method for orthodontists to prescribe and manage their prescriptions and send them directly to the laboratory, but also a laboratory management system for the lab's processing and business transactions.

Figure 1A:
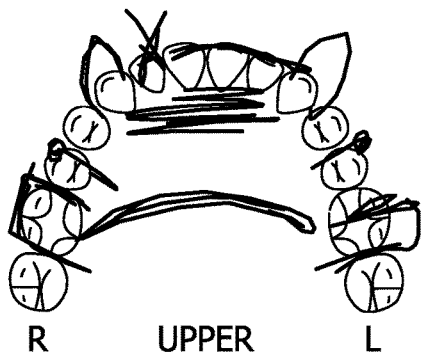
FIGS. 1a-1d are depictions of the graphic portion of a prescription for an orthodontic appliance.
Figure 1C:
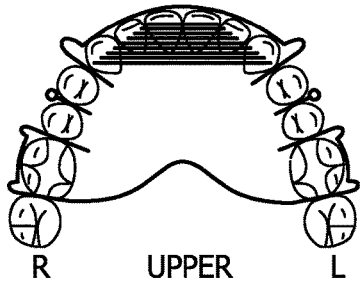
Figure 1B:
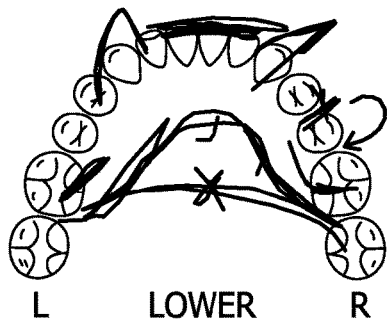
Figure 1D:
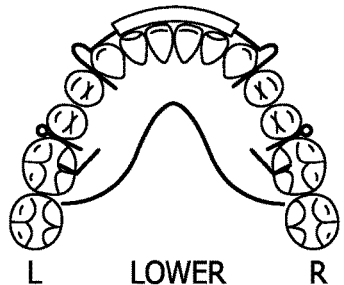

The illustrated system and method can be understood by turning to the prescription as depicted in FIGS. 1a-1d. FIGS. 1a and 1b hand sketches created by an orthodontist for an upper and lower retainer respectively and FIGS. 1c and 1d are the corresponding customized designs created by the doctor on a computer or by a designer in the lab in response to the orthodontist's hand sketched prescription. The prescription can be created in two areas of the system, either directly from a doctor's digital or computer account or manually entered by the lab, if a paper prescription is received. A doctor or his or her staff member, included among the users of the system and method, navigates to a web portal established by the lab via an internet browser and logs into the appropriate account.

The user is presented with the Practice Dashboard 10 for their account as shown in FIG. 2 which outlines what cases are saved, waiting to be submitted to the lab, and those that have already been submitted to the laboratory. Note that the tabs 12, 14 and 16 at the top allow the user to navigate to a patients manager, a template manager, and a prescription manager module respectively.

In order to enter a prescription for a patient, the user first needs to click the patient tab 12 and create a patient profile. Once a patient's profile is created, the user can upload any files associated with the patient or can create a prescription. A prescription can be created from an existing patient's profile. As depicted in FIG. 3 showing the display of the Manage Patients screen 18, the patient profiles includes all the information, from all the patient's prescription to any uploaded files that have been associated in any of the patient's prescriptions. The user may wish to create a prescription by clicking on button 20 and thus be taken to the prescription workspace 22 depicted in FIG. 4.

Figure 4:
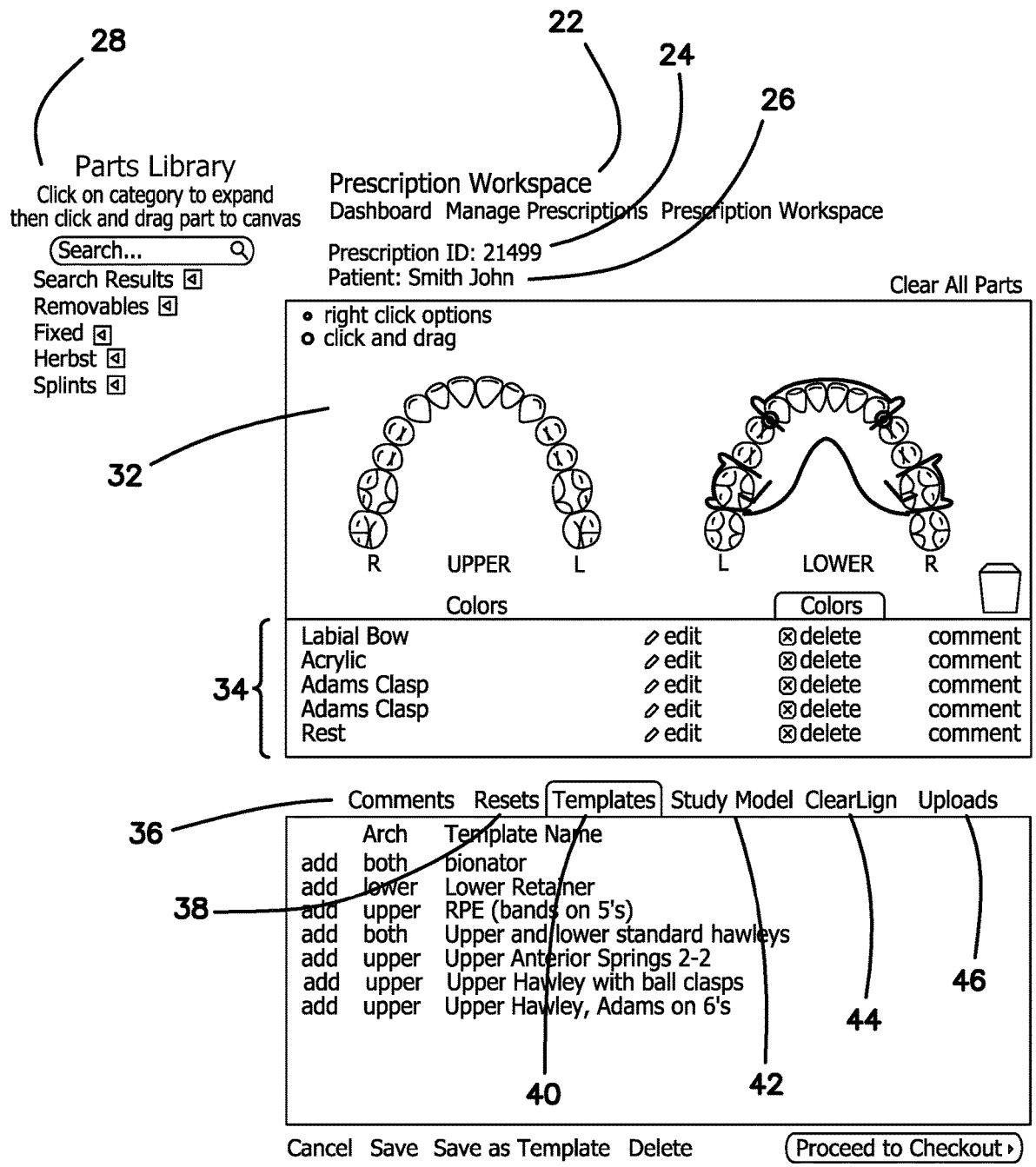
FIG. 4 is an illustrative example of a screen shot of the Prescription Workspace of the illustrated embodiment.

The prescription workspace 22 is the area for any user doing any designing or modification to a prescription. The user interface is very visual and interactive to draw the user into the app. There is the prescription ID 24 which is unique to the prescription and the patient's name 26. On the left edge of the workspace screen is the parts library 28. The user opens the drop down parts listings 30 as illustrated for clasping in FIG. 5 and has the ability to click and drag all the parts of the dental appliance needed to create a complete appliance onto the canvas 32 to the right. Every part is categorized based on the parts category and can be edited from the administrative section which the lab controls. The canvas 32 is the portion of the display where the parts are graphically shown as they populate the design. In the illustration of FIG. 4, a lower retainer is being created in a graphical form, outlining every aspect of design. The user can click and drag any part on the canvas 32 by its blue handle (????) to any area that is anatomically correct. Each part can be customized to only go in certain areas as certain parts would not make sense or appropriate if applied to certain teeth. To enhance customization, the user can right click on a part that has a red dot which enables or displays an option box 48 tailored to that part in those situations as shown in FIG. 6, where that part cannot be represented visually or it is not efficient to do so. The illustrated embodiment of the system disables the browser's right click option to accommodate the right click operation of the application.

Below the canvas 32 is a queue 34 of all the selected parts and below the queue 34 are more action tabs 36-46 as shown in FIG. 7. Comments entered through comment tab 36 are date stamped and marked with the user's name, who is leaving the comment to allow for transparency of who is submitting the comment.

Figure 8:
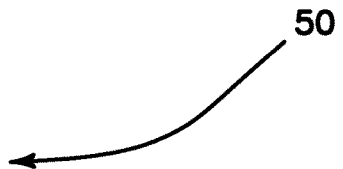
FIG. 8 is an illustrative example of a screen shot of the Resets action tabs provided below the canvas as used in the illustrated embodiment.

The resets tab 38 is a user interface for clinical movement of teeth. The user may click along what is known as the orthodontic crosshatch 50, which is a scientific numbering outline for the teeth as illustrated in FIG. 8. The display is interactive by allowing clicking on the crosshatch 50 to identify what tooth needs to be reset.

The study model tab 42 is made up of check boxes and drop downs (not shown) for clinical study model prescribing, since there is not an efficient way to graphically represent clinical study model prescribing.

The template tab 40 is a useful feature on canvas 32 as illustrated by FIG. 9. The doctor can name and create a template in the template manager 52 and save the design which appears through the use of the template tab 40 below canvas 32. The user finds the template and the user's design automatically loads on the canvas 32. This saves from clicking and dragging all the parts to the canvas 32 which saves significant time in designing.

Figure 10:
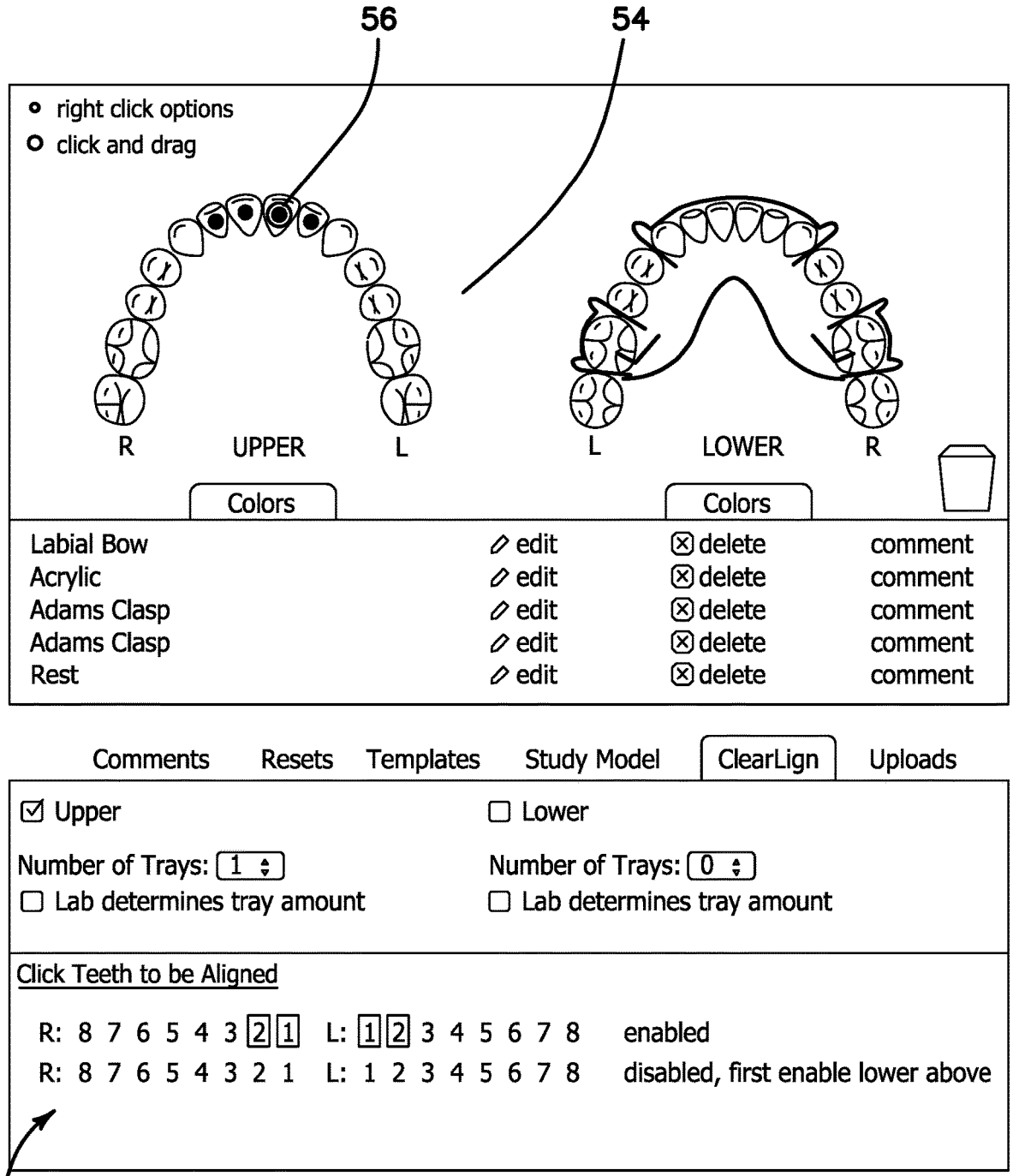
FIG. 10 is an illustrative example of a screen shot of the ClearLign action tabs provided below the canvas as used in the illustrated embodiment.

The clearlign tab 44 is a clear aligner prescription area 54 depicted in FIG. 10. The illustrated embodiment system provides a result similar to the Invisalign® approach, where a plurality of clear trays are manufactured to be applied in a sequence to align the teeth. The crosshatch 50 previously mentioned is used below the clear aligner prescription area 54 in the illustrated embodiment as the doctor picks which teeth to move. A green dot 56 on the teeth is visually present for the technician to fabricate the corresponding tray. The doctor picks how many trays are to be used or allows the lab to make the determination, and the presently illustrated system automatically bills it out properly based on the input.

The upload tab 46 is shown in FIG. 11. A user can click the "add files" button 58 or can click and drag a file or multiple files directly into the drop zone 60 and the file uploads into the prescription from digital three dimensional model files including thumbnail pictures 62 to help diagnose a case. Since everything on the canvas 32 is digital relating to the parts which are dragged into the canvas 32 from the option boxes available, everything has a price attached to it so in essence, the designer of a case is also simultaneously billing the case as the steps of making the design are performed, thereby eliminating the need to have billing manually performed separately by another worker.

Once the case is finished or the customized appliance is completed, the user proceeds to checkout, fills out needed information on the next page about the case and logistics concerning shipping, and then is taken to the confirmation page shown in FIG. 12. The doctor prints out the prescription and sends it with the impression or the cast. At this moment, there is now a digital prescription created and documented. This prescription is now in a queue for cases waiting arrival of the model and impression at the lab.

In another embodiment, the doctor has the ability to create and export a PDF of the prescription for his or her records as shown by activation of button 64 in FIG. 12. With the use of digital scanning, the doctor will upload the digital model, design the appliance, and have the model and the prescription immediately delivered digitally for fabrication, instead a physically delivering an impression. The case is now accessible from the doctor dashboard in the submitted cases queue. This case can always be searched by it's unique ID number 24 or by name 26.

As the case is scanned in at the lab and goes through the process, the dates of interest are populated, such as the estimated ship date, on the prescription. The template manager can be accessed from the template tab 40 at the top of the screen as shown in FIG. 16. It leads the user to the workspace where the doctor can design a template instead and save it for easy retrieval on the workspace when creating a case. The user can edit and delete existing templates as well.

The prescription tab 66 at the top of the screen in FIG. 16 is a queue of all the prescriptions created by the doctor.

In summary, consider now the work flow as facilitated by the illustrated embodiment. When a user logs into a clerical account through accounts tab 68 in FIG. 16 the user is presented with a dashboard which has three queues: Submitted cases (in transit to the lab), checked in cases, and checked out cases related to the user. When a prescription comes to the lab, it is either in the digital printed form as described above, or is written on a traditional prescription for those not engaging in the computerized submission process of the illustrated system, offered under the commercial name, Easyprescription™. Easyprescription™ is used to digitize all prescriptions so a digital workflow tracking takes place. In the case of a written prescription, the data is manually input that otherwise would have been inputted by the doctor creating a new id number 24 and a digital prescription is input through the prescription check-in as shown in FIG. 13. Once the case has been logged in by the clerical account and all the information for the lab has been entered, the case is ready for review of the design if sent in by a doctor, or transferring a design from the paper prescription to the digital prescription. A user logs into the designing account where the designer can review the designs and redesign a case that came in via a paper prescription on the prescription workspace. Changes are made instantly and can be seen by any party who has access to the prescription. The designer has the ability to add charges and discounts to any prescription based on custom orders or a repair that needs a specific amount charged to the case. The designer is now acting as the biller.

Once the design is set, the case travels through the production system. A technician has the ability to log into their technician account where he or she can view cases and his or her designs to produce the needed parts via a monitor and a computer. Cases are scanned by the technician as well into their account for two reasons: 1. To physically track the case throughout the process (where is the case in the lab); and 2. To enable the system to keep track of the production of the employee which can be monitored and used for production metrics via the reporting area in the administrative account.

Once the case is completed it is ready to be check-out as depicted in FIG. 14. The clerical account bar codes the case and checks the case out. That puts the case in a QuickBooks® or accounting queue indicating that it is ready to be exported. The clerical user has the ability to hover the mouse cursor over a case and see the breakdown of the pricing structure in a drop down display as shown in FIG. 15. When all the cases have been scanned and checked out, they will reside in the QuickBooks® queue. The data here can be used to estimate the amount of sales going out as well as provide an organized shipping report. Once the clerical user clicks the "generate file" button, a .csv file is stored within their account which can be downloaded and imported into QuickBooks® via bridge software or directly into QuickBooks®.

The administrative account controls the system and allows the user to make changes to vital portions of Easyprescription™. The user can edit and delete prescriptions as well as patient profiles and run reports on departments and technicians. The user is presented with the same dashboard to see the in-coming cases, the submitted cases, as well as the checked-out cases. The user has the ability to create, edit, and delete all the user accounts within the system. The user has full control over the parts within the system, e.g. the user can change the price as well as how the parts present themselves in the parts library for those working within the workspace through the use of the Manage Parts module 70 as shown in FIG. 16. The user can globally change prices throughout the system and has access to all the prescriptions as well as the patient profiles for any doctor within the system.

The system manufactures dental products or fills orthodontic prescriptions for orthodontic appliances from several hundred parts. Each part has complex movements and several images associated with it. The system uses a native computer language to define each of the parts and their movements. For example, to specify what arches or what teeth onto which a part may move, what sub-parts of a part can be removed in any given instance, how one sub-part moves in relation to another sub-part of the same part, whether a part flips, as with springs, or what options are available to a part comprises a noninclusive listing of some of what constitutes the definition of a part and its movements. Not only does the native computer language define the movements, but with its images it creates a graphic representation of each part. With this native computer language with its definition of the parts, a very comprehensive taxonomy of orthodontic parts and appliances has been assembled. The above software definition of the parts has utility beyond the illustrated embodiments, especially as orthodontic labs work toward integrating CAD and CAM into their workflows.

One of the advantageous features of the illustrated embodiment of the system is that digital three dimensional model files are viewed using the disclosed software system from inside of a browser without installing any local software. There is no need to download software to view three dimensional models. Whether the image file is from an intra-oral scanner, cone-beam or from a digital study model service from a lab, the illustrated system provides a fast and efficient solution to view the files.

EasyRx utilizes a domain-specific language (DSL) or the native computer language for defining part movements and behaviors. An EasyRx part is a representation of an orthodontic appliance that will have different configurations and will be able to be placed in different positions in a patient's mouth. The DSL defines those available configurations and acceptable movements. Only those configurations that have a real-world applicability are allowed.

Figure 17A:
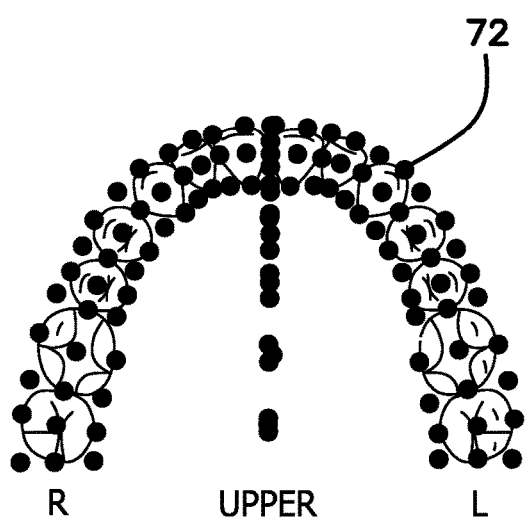
FIGS. 17a and 17b illustrate the magnet points at which anchors may be placed relative to the upper and lower teeth.
Figure 17B:
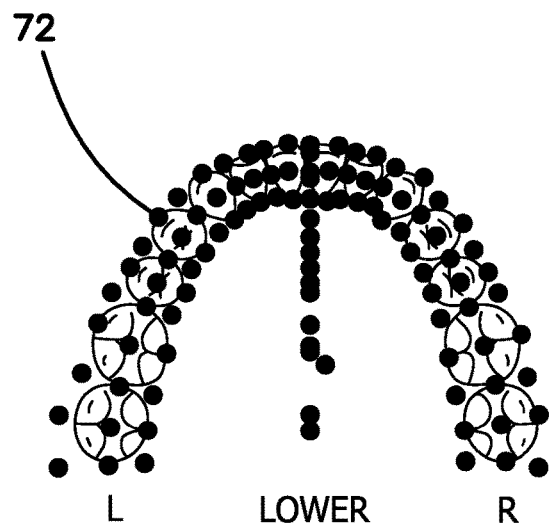

As described above in connection with FIGS. 1*a*-1*d*, a part 71 is drawn on a canvas which consists of two arches of teeth, upper and lower. On those teeth, we define a set of magnet points 72. These are the places at which a part 71 can be positioned as shown by the solid dots in FIGS. 17*a* and 17*b*. Each magnet point 72 has a code that indicates its location on the canvas—its x and y location on the screen and its position related to the teeth—i.e., whether it is on the upper or lower, lingual, labial, or buccal, and so forth.

Figure 18:
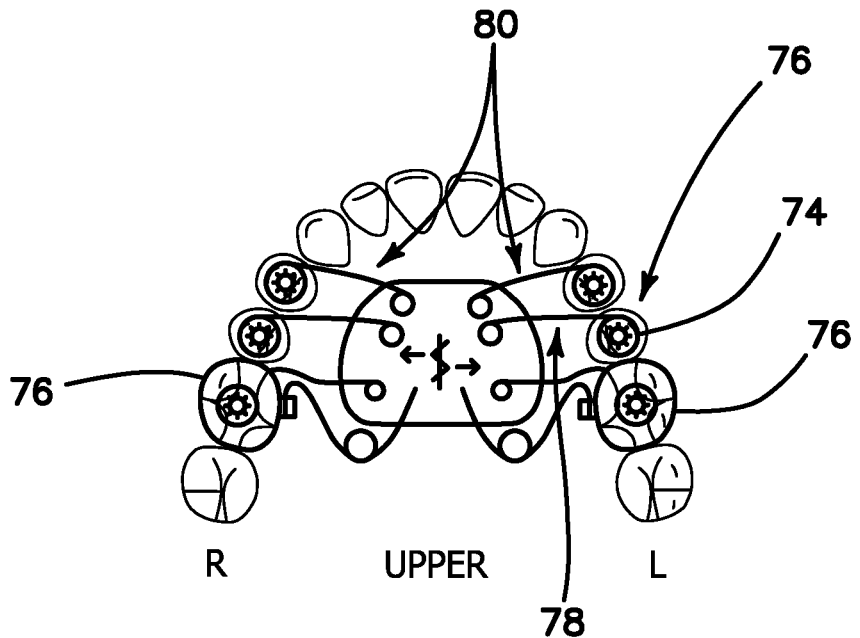
FIG. 18 is a diagram that depicts a design for an orthodontic appliance for an upper set of teeth.

In FIG. 18 each circle 74 is called an anchor 76. Anchors 76 sit on magnet points 72. They are handles that the user can grab to manipulate the part 71. The part 71 can be a bracket, a wire, a pad, a retainer plate or any other kind of dental or orthodontic component. The user clicks on the circle 74 with the mouse and drags the circle 74 to another tooth. The user can also right click and is presented with a list of options that are available to modify the part 71. The anchors 76 are the handles the user grabs to reconfigure the part 71.

Figure 19:
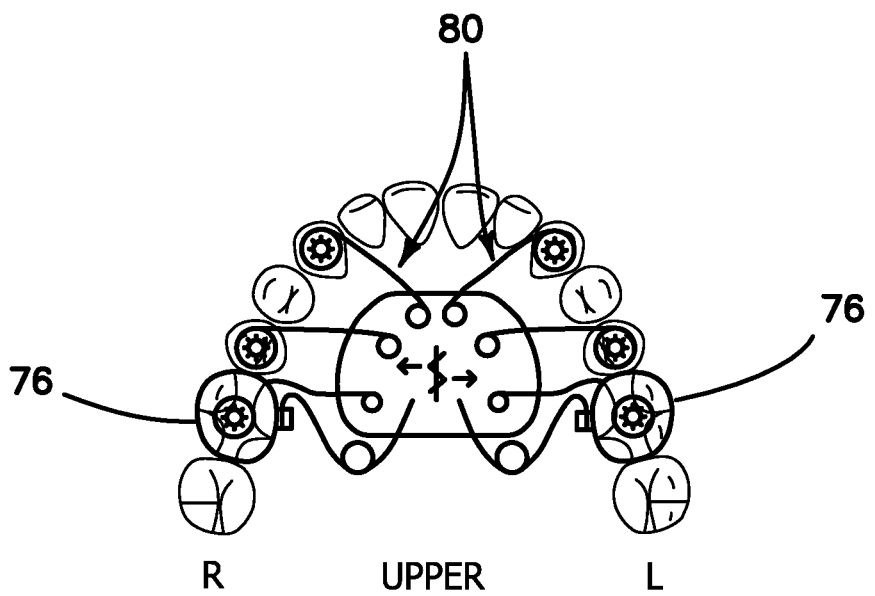
FIG. 19 is the diagram of FIG. 18 wherein the design has been modified using the domain specific language (DSL) of the illustrated embodiments.

FIG. 19 shows the situation where a part 71 that has been reconfigured from the configuration shown for example in FIG. 18. One sub-component 78 in FIG. 18 has been removed, and two others 80 have been moved. Parts can only be reconfigured in very specific ways—e.g., with this part 71 the two anchors 76 toward the back of the mouth cannot be removed or moved. If the user tries to modify them, EasyRx will not allow it. All of these behaviors are defined in the DSL, and EasyRx uses the DSL to put boundaries on the user's manipulation of the parts.

The configurations of FIGS. 17 and 18 is a very simple scenario. EasyRx allows more complex movements and relationships. For example, relationships between anchors 76 can be established whereby one anchor's movement will cause another anchor 76 to move in a given way. Furthermore, the drawing on the canvas can change as an anchor 76 moves from one magnet point 72 to another. Internal system rules are defined to define realities about the parts themselves and how they are used in orthodontic treatment.

Turn now and consider an overview of the DSL implementation. There are two aspects to the EasyRx parts DSL. One allows for the definition of the parts and their behaviors, and the other allows for the application to draw those parts on the canvas and respond to user commands for alteration of the part configuration.

Consider first the DSL and how it defines behaviors. We provide a set of rules into EasyRx for each part 71. When these rules are provided, EasyRx recognizes the existence of the part 71, and allows the user to create a prescription or rule set with it. The rules define the part's behavior, and are specified using the DSL. An example of what the rule for one part 71 looks like in pseudo-code is set forth below.

```
behavior: {
  anchors: [
    0: {
      which_teeth: 4-7,
      side: UL,
      starting_location: 6UL,
      color: Green,
      which_drawing: 9032,
    },
    1: {
      which_teeth: 4-7,
      side: UR,
      starting_location: 6UR,
      color: Green,
      which_drawing: 9032,
    },
  ],
  anchor_buddies_allowed_positions: [
    {
      anchors_buddy: 0 → 1,
      rules: {
        1: [1], 2: [2, 1], 3: [3, 2], 4: [3], 5: [4]
      }
    }
  ],
  forced_move: [ ... ],
  anchors_pair_across_arch: [ ... ]
},
options: {
  transform: { ... },
  transform_1: { ... },
  transform_2: { ... },
  transform_3: { ... },
  ...
  transform_9: { ... },
  color: { ... },
},
place: function ( ) { ... },
update: function ( ) { ... }
```

Note the behavior section, which defines what anchors 76 a part 71 has, what drawings are associated with each anchor 76, how and to where the anchor 76 moves, and how its movements affect other anchors 76.

First we define the set of anchors 76 that comprise the part 71. Each anchor 76 has a range of magnet points 72 it can sit on or at which it can be positioned. For example, we might define an anchor 76 that can sit on all the upper arch magnet points 72 on teeth 1-4 (counting from the front of the mouth back). We then associate a drawing with that anchor 76, one for each position that the anchor 76 can sit in. Along with the anchor definition, we define the color of the drawing associated with that anchor 76. Finally, we also define whether the anchor 76 can be removed. This allows subparts of parts 71 to be pulled off the canvas.

If we need to have one anchor's position influence another anchor's position, we define that relationship next by setting up forced moves 82, anchor buddies 84 and anchor pairs 86. Each one establishes a different relationship between the anchors 76. Forced moves 82 allow any anchor 76 to be moved to a specific magnet point 72 when the current anchor 76 is on a specific magnet point 72. Anchor buddies 84 are used to keep the positions of two anchors 76 within a certain distance of each other. Anchor pairs 86 are used to pair two anchors 76 across the arch 88, one on the left side and one of the right side. When the left side moves to a certain magnet point 72, the right side will be moved with it.

Figure 20A:
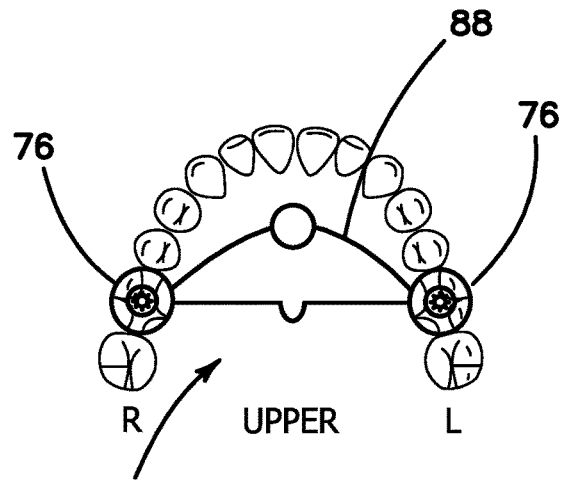
FIGS. 20a and 20b are diagrams showing the modification of another design using the domain specific language (DSL) of the illustrated embodiments.
Figure 20B:
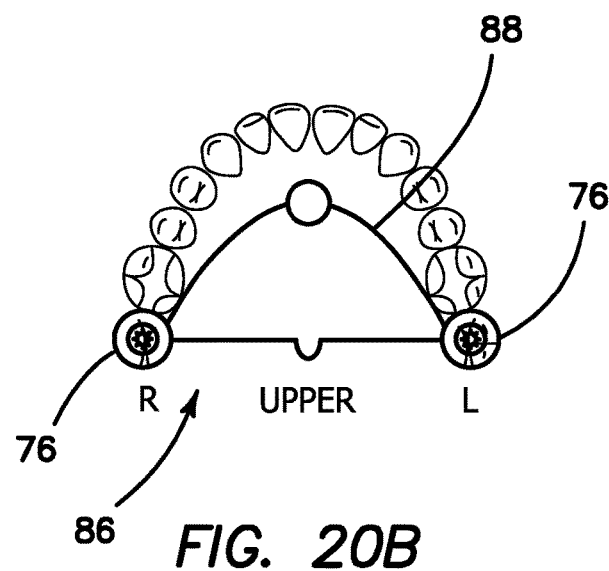

FIGS. 20*a* and 20*b* illustrate an example of a part 71 with anchors 76 paired across the arch 88 in an anchor pair 86. Whenever the anchor 76 on the left or right is moved, the anchor 76 on the other side is moved with it as shown by comparison of FIG. 20*a* to FIG. 20*b*.

Figure 21A:
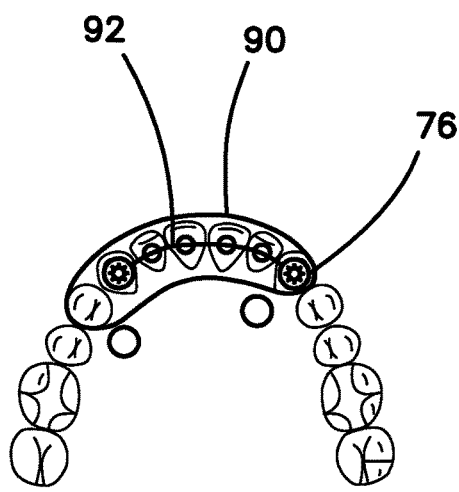
FIGS. 21a and 21b are diagrams showing the modification of yet another design using the domain specific language (DSL) of the illustrated embodiments.
Figure 21B:
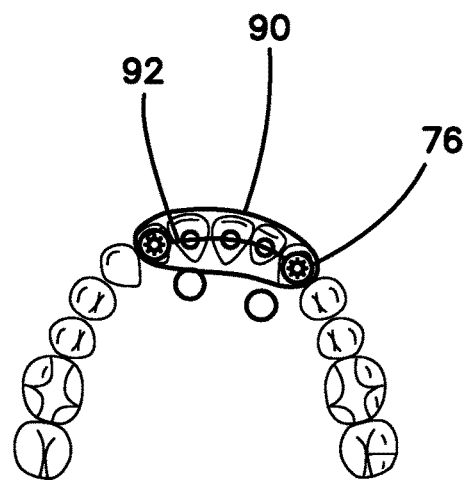

FIGS. 21*a* and 21*b* is an example of anchor buddies 84. Whenever the anchor 76 that controls the tray 90 is moved the wire 92 moves too, and vice versa as can be verified by comparison of FIG. 21*a* and FIG. 21*b*, where one tooth has been removed from tray 90. This is done because the tray 92 contains the wire 92 within it.

Figure 22:
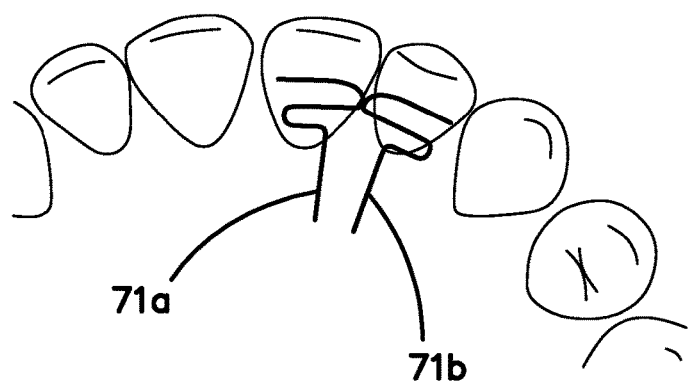
FIG. 22 is a diagram showing the transformation of a part between two different orientations of a design using the domain specific language (DSL) of the illustrated embodiments.

The second aspect handles transformations of the part's appearance on the canvas or its orientation with respect to the teeth or other parts. For example, certain parts flip across the x axis, and those flips are defined here. In FIG. 22, the part 71*a* on the right is the same as the left part 71*b*, but it has been transformed with an optional flip to make it face the opposite way.

The transformations are defined by specifying to which of the parts' anchors 76 the transform applies and the setting the result of the transformation, e.g., whether the transform removes the anchor 76, changes the drawing, or something else.

Consider now the DSL movement. The final two lines in the listing of pseudocode above, "place" and "update", control the part's movements while the user is interacting with the part 71. The function codes "place" and "update" consume the behavior rules, draw the images on the canvas, and create the listeners or receiving software modules to respond to user input. Whenever a user moves one of the anchors 76, the update function checks the rule set, which we make executable for performance, and if any changes need to be made, e.g., if an anchor 76 was moved and as a result an anchor buddy 84 needs to be moved, the update function makes those changes. The update function also prevents the user from putting an anchor in a place it cannot be placed according to the behavior section of the part's definition.

Consider the significance of the DSL. Using this method, we define 355 or more different orthodontic parts. As part of that definition we have a catalog of how all those parts behave. We can ask, for example, whether a given part 71 can ever be placed on a certain tooth. Or if we place the left side of the part 71 on a given tooth, on what teeth it is allowed to be placed across the arch 88 on the right side. Essentially, it is a taxonomy of orthodontic parts with the rules for their behavior. This set of rules has utility beyond EasyRx. It can be used by any software that needs to place orthodontic parts on teeth and needs to know which teeth can receive which parts. It is not tied to any specific method of display.

The illustrated embodiments of the system and method can now be understood as an overall prescription management system and method designed to run the logistics of an orthodontic lab while allowing doctors access to submit, store, and review all their prescriptions. The system allows for flexibility to make customizations based on the particular lab using the system. Multiple users of the system provide input through prescription, design and fabrication phases, which activities simultaneously creates a digital tracking and document record of the case and automatic billing. Since this is a web based system, updates can be made on the fly and the labs' data as well as the doctors' data is stored via the cloud.

Many alterations and modifications may be made by those having ordinary skill in the art without departing from the spirit and scope of the embodiments. Therefore, it must be understood that the illustrated embodiment has been set forth only for the purposes of example and that it should not be taken as limiting the embodiments as defined by the following embodiments and its various embodiments.

Therefore, it must be understood that the illustrated embodiment has been set forth only for the purposes of example and that it should not be taken as limiting the embodiments as defined by the following claims. For example, notwithstanding the fact that the elements of a claim are set forth below in a certain combination, it must be expressly understood that the embodiments includes other combinations of fewer, more or different elements, which are disclosed in above even when not initially claimed in such combinations. A teaching that two elements are combined in a claimed combination is further to be understood as also allowing for a claimed combination in which the two elements are not combined with each other, but may be used alone or combined in other combinations. The excision of any disclosed element of the embodiments is explicitly contemplated as within the scope of the embodiments.

The words used in this specification to describe the various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the embodiments.

We claim:

1. A method for controlling a design in a computer for an assembly of a plurality of orthodontic parts in an orthodontic appliance by a user comprising:
   defining a rule set related to permissible movement and behavior for each one of the plurality of orthodontic parts with respect to at least one tooth or other one of the plurality of orthodontic parts;
   moving, placing, orienting or removing at least one of the plurality of orthodontic parts in a graphic image of the design by the user according to the defined rule set for the at least one of the plurality of orthodontic parts during the assembly of the design of the orthodontic appliance; and
   simultaneously creating an automatic billing at the same time as moving, placing, orienting or removing the at least one of the plurality of orthodontic parts in the graphic image of the design according to the defined rule set for the at least one of the plurality of orthodontic parts during the assembly of the design of the orthodontic appliance,
   wherein simultaneously creating an automatic billing at the same time as moving, placing, orienting or removing the at least one of the plurality of orthodontic parts in the graphic image of the design comprises creating and updating an itemized queue of the plurality of orthodontic parts and their respective pricing automatically in real time as each orthodontic part is moved, placed, oriented, or removed from the graphic image of the design during the assembly of the design of the orthodontic appliance.

2. The method of claim 1 further comprising converting the design as assembled into computer assisted manufacturing instructions to assemble the orthodontic appliance from the plurality of orthodontic parts.

3. The method of claim 1 where defining a rule set related to permissible movement and behavior for each one of the plurality of orthodontic parts with respect to at least one tooth or other one of the plurality of orthodontic parts comprises:
   defining at least one anchor for each one of the plurality of orthodontic parts and a plurality of magnet points at which the at least one anchor may be positioned;
   defining whether or not the at least one anchor can be removed from the design;
   defining whether the at least one anchor is one of two anchor buddies or an anchor pair with coupled movement with another anchor; or
   defining an orientation of each one of the plurality of orthodontic parts.

* * * * *